United States Patent
Yu et al.

(10) Patent No.: US 11,583,926 B2
(45) Date of Patent: Feb. 21, 2023

(54) FIELD SHAPING DEVICE FOR RADIATION THERAPY

(71) Applicant: The Board of Trustees of the Leland Stanford Junior University, Stanford, CA (US)

(72) Inventors: Shu-Jung Yu, San Jose, CA (US); Lawrie Basil Skinner, Redwood City, CA (US); Benjamin Pooya Fahimian, Menlo Park, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 406 days.

(21) Appl. No.: 16/809,427

(22) Filed: Mar. 4, 2020

(65) Prior Publication Data
US 2020/0290119 A1    Sep. 17, 2020

Related U.S. Application Data

(60) Provisional application No. 62/816,599, filed on Mar. 11, 2019.

(51) Int. Cl.
| | |
|---|---|
| *B22F 10/10* | (2021.01) |
| *B29C 64/141* | (2017.01) |
| *B33Y 50/00* | (2015.01) |
| *B33Y 10/00* | (2015.01) |
| *B33Y 70/00* | (2020.01) |
| *A61N 5/10* | (2006.01) |
| *B33Y 80/00* | (2015.01) |

(52) U.S. Cl.
CPC .......... *B22F 10/10* (2021.01); *A61N 5/10* (2013.01); *B29C 64/141* (2017.08); *B33Y 10/00* (2014.12); *B33Y 50/00* (2014.12); *B33Y 70/00* (2014.12); *B33Y 80/00* (2014.12); *A61N 2005/1094* (2013.01)

(58) Field of Classification Search
CPC ......... B22F 10/10; B33Y 10/00; B33Y 50/00; B33Y 70/00; B33Y 80/00; B29C 64/141; A61N 5/10; A61N 2005/1094
USPC .................................................. 250/515.1
See application file for complete search history.

(56) References Cited

U.S. PATENT DOCUMENTS

| | | | |
|---|---|---|---|
| 7,741,624 B1 * | 6/2010 | Sahadevan | ........... A61N 5/1081 250/341.7 |
| 2016/0289468 A1 | 10/2016 | Turner | |

OTHER PUBLICATIONS

Kinsaraa et al., "Characterization of Attenuating Properties of Novel Composite Radiation Shields," Nucl Med Radiat Ther 2016, 7:6, DOI: 10.4172/2155-9619.1000316 (Year: 2016).*

(Continued)

*Primary Examiner* — Matthew J Daniels
*Assistant Examiner* — Gregory C. Grosso
(74) *Attorney, Agent, or Firm* — Lumen Patent Firm

(57) ABSTRACT

A radiation beam field shaping device is made from a 3D printed frame that contains and gives shape to a granular material with bulk density of at least 3 g/cm³ and composed of metal grains having a size between 1 μm and 4 mm. The frame has a hole in the bottom with surrounding walls that defines the desired beam shape. In one implementation, the metal grains are composed of solid tungsten alloy ball bearings and/or tungsten alloy powder.

6 Claims, 5 Drawing Sheets

(56) References Cited

OTHER PUBLICATIONS

Michiels et al. Production of patient-specific electron beam aperture cut-outs using a low-cost, multi-purpose 3D printer. J Appl Clin Med Phys 2018; 19:5:756-760.
Skinner et al., Tungsten filled 3D printed field shaping devices for electron beam radiation therapy, PLoS ONE 14(6): e0217757, Jun. 19, 2019.
Kijima et al., The Shielding Ability of Novel Tungsten Rubber Against the Electron Beam for Clinical Use in Radiation Therapy, Anticancer research 38(7):3919-3927 • Jul. 2018.
Yue et al., A new lead-free radiation shielding material for radiotherapy. Radiat Prot Dosimetry. Feb. 2009;133(4):256-60.
Tajiri et al., A new radiation shielding block material for radiation therapy. Med Phys. Nov. 2004;31(11):3022-3.
Lee et al., A depth-sensing technique on 3D-printed compensator for total body irradiation patient measurement and treatment planning. Med Phys. Nov. 2016; 43(11): 6137-6144. Published online Oct. 27, 2016.
Zemnick et al., Rapid prototyping technique for creating a radiation shield. J Prosthet Dent. Apr. 2007;97(4):236-41.

\* cited by examiner 3D printed

— measured
······ planned

Cerrobend

— measured
— — shifted
······ planned

FIELD SHAPING DEVICE FOR RADIATION THERAPY

CROSS-REFERENCE TO RELATED APPLICATIONS

This application claims priority from U.S. Provisional Patent Application 62/816,599 filed Mar. 11, 2019, which is incorporated herein by reference.

FIELD OF THE INVENTION

The present invention relates generally to radiotherapy. More specifically, the invention relates to radiation shielding devices for shaping the field in radiation beams.

BACKGROUND OF THE INVENTION

Electron beam radiotherapy delivers a beam into a field of view to irradiate a tumor. To avoid harming healthy tissue, it is desirable to restrict the radiation beam to a specific region of tissue where the tumor is located. This is accomplished by modifying the beam shape using radiation shielding devices, also called field shaping devices. Because the tumor shape and size for each patient is unique, shielding devices with patient-specific shapes are cast into customized molds in accordance with an outline specified by a treatment planning system (TPS). Once molded, the customized solid field shaping device may be mounted to a blocking tray to facilitate correct positioning relative to the treatment beam.

Creating these custom field shaping devices is labor intensive and complicates the treatment procedure. Moreover, traditional radiation shielding materials such as lead are difficult to mold due to their melting points (over 300 C) and poor mechanical properties. To facilitate molding, a commonly used material is a low melting point alloy of 50.0% bismuth, 26.7% lead, 13.3% tin, and 10.0% cadmium, which is variously known as Wood's metal, Lipowitz's alloy, or Cerrobend. However, creating customized Cerrobend field shaping devices using the conventional molding process remains labor intensive and dangerous because the lead and cadmium in Cerrobend make it highly toxic.

In addition, the conventional multi-step molding process for creating custom Cerrobend field shaping devices results in field shape and placement uncertainties of several millimeters. These errors are introduced when transferring the outline from the treatment planning system (TPS) to the cutting tools. As an example of this type of error, FIG. 1A shows the measured light field edge 100 from a typical clinical Cerrobend insert with a mean deviation of 2.6±0.2 mm compared to the planned outline 102. Even after shifting, the shifted Cerrobend outline 104 still shows a maximum deviation of 2 mm and a mean of 0.8 mm compared to the planned outline 102.

There are two major reasons for the inaccuracy of the Cerrobend cutout shown in FIG. 1A. One reason is that the melt casting and cutting of the foam mold themselves include some imprecision. More importantly, the other reason for inaccuracy is the placement error: a foam casting mold is manually placed to form the Cerrobend. This placement inaccuracy is significant because it limits accurate alignment of the electron field with the kV imaging x-rays and MV treatment x-rays.

One approach to simplify the creation of Cerrobend field shaping devices is to use fused deposition modelling (FDM) 3D printers to create 3D printed plastic parts to create silicone or plaster molds, which in turn are used to cast Cerrobend into the mold. This multistep process, however, is labor intensive and still suffers from problems from accuracy. It also does not solve the problem with Cerrobend toxicity.

BRIEF SUMMARY OF THE INVENTION

The present description provides a field shaping device for radiotherapy applications and method of making the same. The device is composed of a 3D printed patient-customizable shell/frame filled with a layer of granular material, such as metal ball bearings or metal powder. The 3D printed frame has walls that hold and form the granular material in a customized shape. Although 3D printed techniques have been used previously in the process of making customized field shaping devices, their use has been limited to creating a temporary mold to be used only in a molding process, after which the 3D printed mold is discarded, resulting in an end product composed of a single solid metal or solid metal composite field shaping device. Devices according to the present invention, in contrast, include the 3D printed frame, as it actively functions to hold and give shape to the granular material that attenuates the radiation.

The current invention also provides an improved method of making a radiation beam shaping device. The method is simpler and more precise than existing methods, as it avoids entirely the need for an intermediate molding step. It also avoids the use of toxic radiation attenuating materials. This method allows accurate field shaping using standard applicators. The all-digital workflow ensures accuracy and reproducibility of the inserts. The 3D printed cutout is designed digitally, and its manufacture does not include placement error, manual cutting or melt casting. The method provides more accurate electron radiotherapy with reduced toxicity, labor, and cost compared to traditional Cerrobend methods, and provides improved reproduction of the field placement and field shape compared to Cerrobend and integration with multi-leaf collimator (MLC) technologies.

According to one aspect, the invention provides a radiation beam field shaping device comprising: a frame having a bottom, outer side walls, an opening in the bottom, and inner walls around the opening in the bottom, where the outer side walls, bottom, and inner side walls define an interior space of the frame; and a granular material contained within the interior space, where the granular material has a bulk density of at least 3 g/cm$^3$ and composed of metal grains having a size between 1 μm and 4 mm.

Preferably, the frame is composed of a 3D printable material with Youngs modulus greater than 0.5 GPa.

In one implementation, the inner side walls are 0.2-5 mm thick and 5-30 mm tall.

In one implementation, the granular material contained within the interior space forms a 5-30 mm thick layer.

In one implementation, the metal grains are solid tungsten alloy ball bearings 1-4 mm in diameter.

In one implementation, the metal grains are composed of a powder selected from the group consisting of tungsten alloy powder and aluminum oxide powder.

In another aspect, the invention provides a method of making a radiation beam field shaping device, the method comprising: 3D printing a frame having a bottom, outer side walls, an opening in the bottom, and inner walls around the opening in the bottom, where the outer side walls, bottom, and inner side walls define an interior space of the plastic frame, where the opening has a shape specified by data export from a treatment planning system; and filling the interior space with a granular material having a bulk density of at least 3 g/cm³ and composed of metal grains having a size between 1 μm and 4 mm.

DETAILED DESCRIPTION OF THE INVENTION

Figure 4:
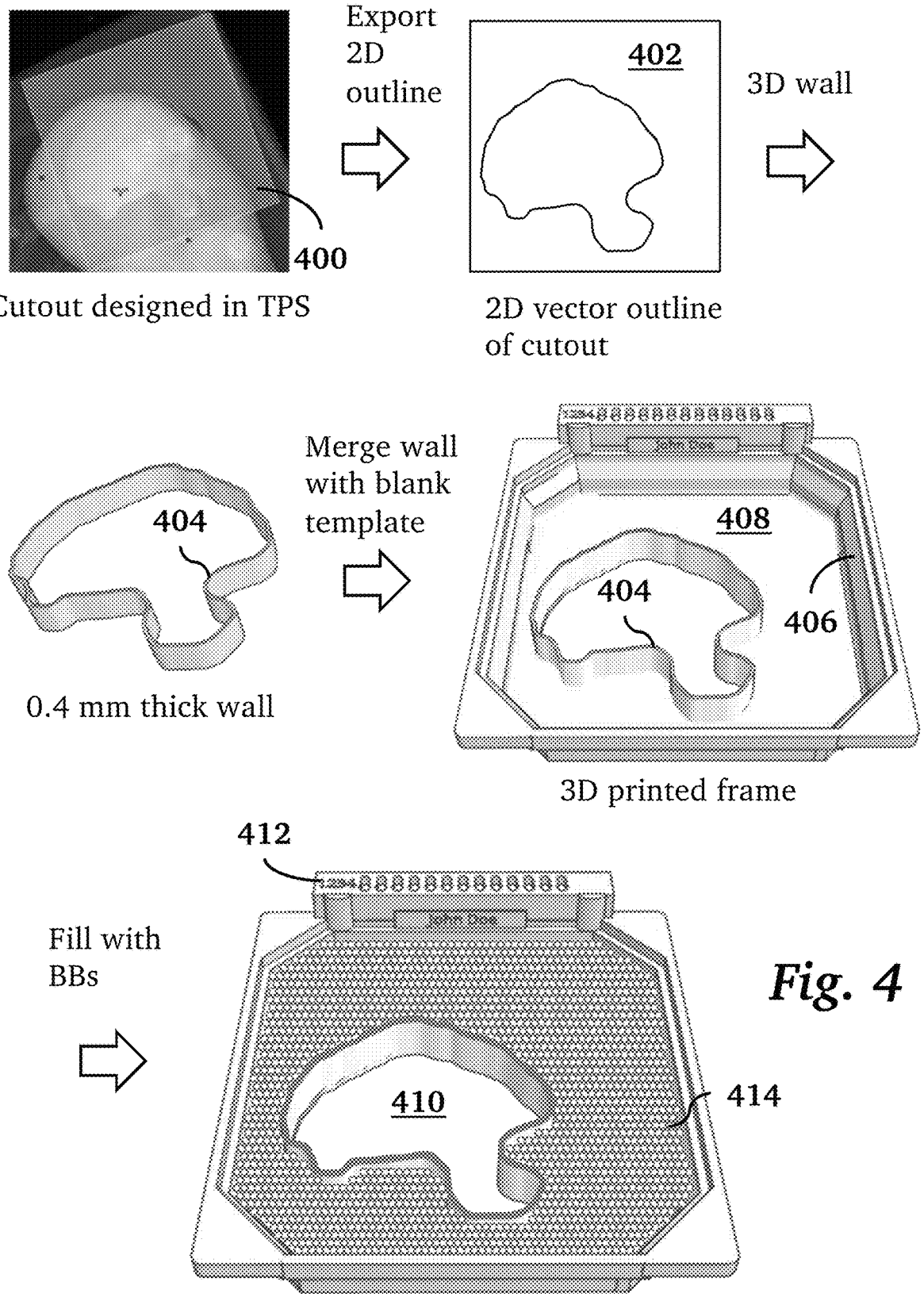
FIG. 4 is a schematic diagram illustrating a workflow for making a field shaping device according to an embodiment of the invention.

FIG. 4 shows an electron field shaping device and workflow for making such a device, according to an embodiment of the invention. First, the field outline 400 is exported from a treatment planning system and converted into a 2D vector image 402. The 2D outline is then imported in to CAD software and extruded into a 3D wall 404 using a 3D printer. Divergence and edge rounding fillets are also included in this step. The field edge wall 404 is then combined with a 3D printed template outline that has a corresponding hole 410 in its bottom surface 408. The template also has outer walls 406. Thus, the finished frame has a bottom 408, outer side walls 406, an opening 410 in the bottom 408, and inner walls 404 around the opening in the bottom. The outer side walls, bottom, and inner side walls define an interior space of the frame enclosed on all sides except the top. In preferred implementations, the inner side walls are between 0.2 mm and 5 mm thick and between 5 mm and 30 mm tall.

Patient identifiers and custom codes 412 can be imprinted directly into the final 3D printed frame. The 3D printed insert code is more reliably read by code readers than the standard inserts; the 3D printed tray is a single part and is made to tighter tolerances. This avoids inconsistency of the code readers and inserts with conventional cutouts that causes treatment delays and inconvenience to patients. The imprinted name on the device also provides an intuitive way for the therapists to check the cutout before the treatment.

The frame is preferably 3D printed in a single step as one part, i.e., the field edge wall is printed at the same time as the rest of the frame. Preferably, the frame is printed at 45 degrees to the frame outer walls, which makes the structure stronger than printing at 0 degrees. The 3D printed shell can be optimized to print unattended in 2-5 hours, on standard commercial 3D printers. The 3D printing process requires only approximately 5-15 minutes of labor to fill, clean up, and verify the printed cutout.

Production workflow of the cutouts is streamlined by using a blank digital template for each applicator size. The template includes the encoder strip and tray insert shape that mates with the applicator cone. To create the single custom part, the template is digitally aligned and merged with the desired field outline shape. The field outline is generated, for example, by exporting from the Eclipse TPS (Varian, Palo Alto, Calif., USA) into a PDF file. Instead of creating a physical printout, as done in the conventional Cerrobend process, the outline is digitally traced and saved as a 2D vector file. This 2D outline is then taken into 3D design software (Autodesk fusion360, San Francisco, Calif., USA) expanded and extruded to create a thin wall of 0.4 mm in thickness and 15 mm in height (3 mm of which are taken by the base and lid). This field shape part is then digitally aligned and combined with the blank tray template into a single part.

The 3D printed frame is designed to fit clinical electron applicators, using freely available CAD software (e.g., TinkerCAD, Fusion360, inkscape), and are printed using a commercial 3D printer (e.g., Ultimaker 2+). The printing material in one implementation is polylactic acid (PLA) plastic. PLA is chosen for printing material due to its abundance, ease of use, and low cost for rapid prototyping.

Many 3D printable materials may be used for the frame, provided they have sufficient strength and toughness to hold the granular shielding material. Soft materials such as thermoplastic elastomers (TPE) and thermoplastic polyurethanes (TPU) would not be suitable. PLA is sufficiently robust and can be easily modified to add strength as needed. A benefit of 3D printed parts is that if they break, they can be accurately reproduced within a few hours with minimal additional labor. If desired, stronger, and more heat resistant plastics can be used. Preferably, the material has a Youngs modulus more than 0.5 GPa. Example materials include polylactic acid, carbon fiber reinforced nylon, or polycarbonate or polyethylene terephthalate (PET) based plastics, polyamide, acrylonitrile butadiene styrene, high impact polystyrene, and resin. It is also possible to 3D print the frame in metal or carbon fiber. In the present context, 3D printing is defined to encompass various technologies including fused deposition modeling, stereolithography, melt-extrusion, laser sintering, UV-hardening.

The completed 3D printed frame is filled with a layer of granular metal material 414, e.g., metal ball bearings (BBs) or metal powder. For example, the granular metal material may be composed of 2 mm diameter tungsten alloy BBs (THPP, San Diego Calif.) with a nominal density of 17.5 g/cm³. Tungsten alloys are preferred due to their high electron density, low toxicity, and reasonable cost.

In the present document, a granular material is defined to be a collection of discrete solid, particles (called grains) at least 1 μm in size that are free to move relative to each other, i.e., the individual particles are not chemically bound to each other or otherwise fixed in position relative to each other, e.g., by being embedded in a resin or other solid matrix material. Powders, which are a sub-class of granular materials, are defined to be a dry, bulk solid composed of many fine particles that may flow freely when shaken or tilted. To emphasize that the grains making up the granular material are not bound to each other or otherwise fixed within a rigid matrix, the granular material may also be called a loose granular material. In some embodiments of the invention, the granular material may be composed of metal BBs or metal powder. Preferably, the BBs have a diameter between 1 mm and 4 mm. Preferably, the grain size of the powder is at least 1 μm. When using powders, standard lab practices are recommended for safety.

In some embodiments, the grains can have different sizes. For example, the granular material can include a combination of BBs of different sizes, or a combination of BBs and a powder that fills the gaps between the BBs. This achieves higher density than the BBs alone. In a preferred embodiment, a combination of tungsten alloy BBs and tungsten alloy powder provides high density at low cost without toxic materials.

To be suitable for radiation shielding, the granular metal material 414 should have a minimum bulk density of 3 g/cm³, but more preferably has a higher bulk density of 10 g/cm³ or more. Generally, lower density materials result in a thicker cutout and will less effectively block Bremsstrahlung from the linear accelerator's head. To achieve high density, the metal grains are preferably composed of a metal or metal alloy with high atomic number. Such materials allow for thinner layers of the granular material and sharper beam edges. Examples of preferred metal powders include tungsten, tungsten alloys, and aluminum oxide powders. Although aluminum oxide powder has an atomic number significantly less than tungsten, its octahedral arrangement gives it a reasonable density of 4 g/cm³. It has the advantage of reducing x-ray contamination of the electron beam, at the expense of blurrier beam edges than denser materials. Examples of preferred metal BBs are tungsten alloy BBs and brass BBs. Using tungsten alloy BBs (17.5 g/cm³) with a packing fraction of 0.6 yields a bulk density of 10.5 g/cm³. This density was achieved with no attempt to maximize the number of BBs in the volume. They were poured in without any pressing, or rearrangement.

Among high atomic number elements, tungsten is a preferred metal for the granular material. Of the non-toxic materials with higher electron densities than tungsten (z=74) there is only rhenium, osmium, iridium, platinum, and gold (z=75-79), all of which are prohibitively expensive. Elements with z=80 (mercury) or greater are not suitable because they have either chemical toxicity or radioactivity.

Machined brass is another material that may be used. It has comparable electron density to lead, but with lower z, and hence lower Bremsstrahlung production. There are two main drawbacks to using lower density materials for electron field shaping: (i) the increased cutout thickness results in broader penumbra, and (ii) the lower x-ray absorption of lower density materials means they are less able to shield Bremsstrahlung x-rays produced up stream of the cutout, or those generated in the cutout itself. When considering Bremsstrahlung it is important to note that, 70-90% of the Bremsstrahlung of a typical electron beam therapy is generated in the linac head (e.g. scattering foils), not the final Cerrobend aperture. This means that the ability of the cutout to absorb head-generated Bremsstrahlung should be considered as well as the Bremsstrahlung that the cutout itself generates. The lower relative Bremsstrahlung of tungsten alloy compared to Cerrobend, due to its lower z, demonstrates that it should produce less Bremsstrahlung than standard Cerrobend cutouts.

Table 1 lists relevant physical properties of materials of interest for the granular material. The "particle ρ" column represents the bulk packed density of that material in a powder or ball bearing form. Relative electron density is the number of electrons per unit volume relative to water.

A quality assurance (QA) procedure was developed to ensure the cutout is correctly filled and printed. The printed insert is first visually inspected to make sure there is no major defect. The proper filling with the granular material is measured the by weight of the cutout using Eq. 1:

$$W_{tot} \geq V_{BB} \cdot pf \cdot \rho_{BB} + W_{ins}. \quad \text{(Eq. 1)}$$

where $W_{tot}$ is the expected weight, $V_{BB}$ is the volume of the insert available for the granular material, obtained from the 3D files, $\rho_{BB}$ is the density of the grains (e.g., tungsten BBs have a density of 17.5 g/cm³), pf is the packing fraction and $W_{ins}$ the weight of the insert. Here we use the minimum acceptable pf=0.6.

The weight, $W_{tot}$, was measured using a digital scale calibrated using standard weights to within 0.1%. To pass the QA, the measured weight should satisfy Eq. 1. Field shape verification was performed by overlaying the cutout with a transparent printout from the TPS on transparent paper to compare the shape of the cutout. The 3D printing process, standard printing profiles and procedures should be used to ensure consistency. Attention should be paid to the first layer of each print as if this does not fully stick to the print bed it can cause distortion.

Figure 1B:
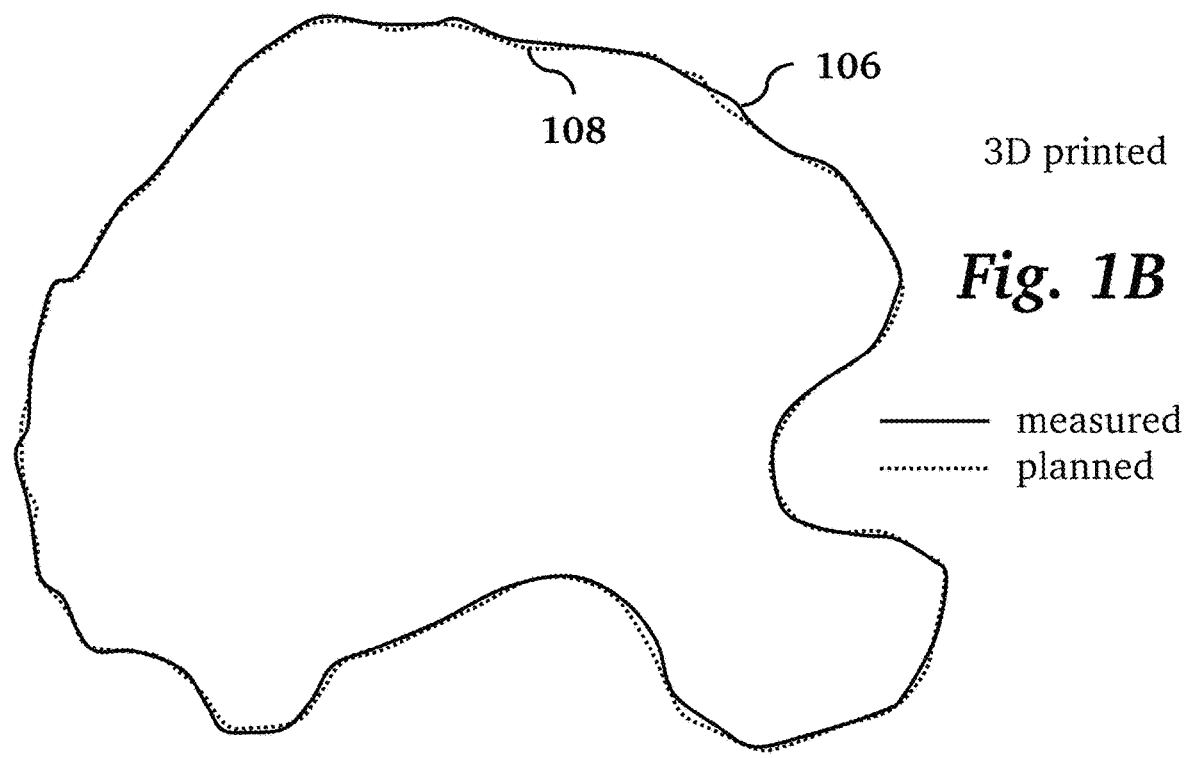
FIG. 1A-1B illustrate the deviation from planned field shaping outlines with measured Cerrobend device outlines (FIG. 1A) and measured outlines of a device according to the present invention (FIG. 1B).
Figure 1A:
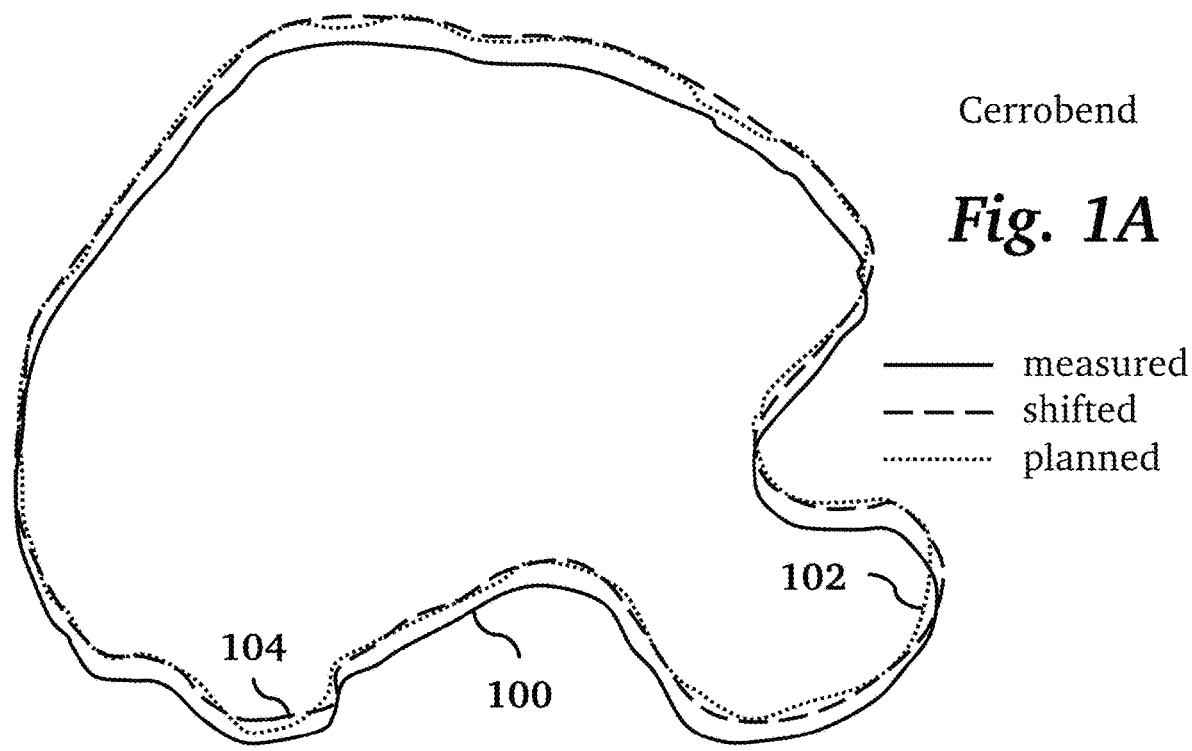

In one experimental test, 3D printed plastic frames were fabricated using the methods described above, and each was filled with layer of 2 mm diameter tungsten BBs. The light field edge of the field shaping device was measured when mounted in an electron applicator on a linear accelerator (Varian, Palo Alto, Calif., USA). FIG. 1B shows the measured field shape 106 compared to the planned field shape 108. The measured outline 106 of the 3D printed device follows the planned outline 108 with maximum deviation of 1 mm and a mean of 0.4 mm. By comparison, FIG. 1A shows the measured field shape of a conventional Cerrobend field shaping device compared to the planned fields. The planned outline 102 and the measured outline 100 have a mean deviation of 2.6±0.2 mm. Even after shifting, the shifted Cerrobend outline 104 shows a maximum deviation of 2 mm and a mean of 0.8 mm compared to the planned outline.

TABLE 1

| material | Composition | <z> | Relative Bremsstrahlung | Relative electron density | Solid ρ g/cm³ | particle ρ g/cm³ |
|---|---|---|---|---|---|---|
| Tungsten alloy | $W_{24}Ni_4Fe_2$ | 64 | 0.90 | 9.67 | 17.5 | 10.5 |
| Lead | Pb | 82 | 1.15 | 5.98 | 11 | — |
| Woods metal (Cerrobend) | $Bi_{19}Pb_{10}Sn_9Cd_7$ | 71 | 1 | 5.08 | 9.7 | — |
| Brass | CuZn | 29.5 | 0.42 | 5.47 | 8.96 | 5.4 |
| Steel | $Fe_3C$ | 21 | 0.30 | 5.05 | 8.05 | 4.8 |
| $Al_2O_3$ (Ceramic/Sapphire) | $Al_2O_3$ | 10 | 0.14 | 2.60 | 3.95 | 2.37 |
| PLA (plastic) | $C_3H_4O_2$ | 4.2 | 0.06 | 1.03-1.2 | 1.2-1.4 | — |
| PMMA (Lucite) | $C_5O_2H_8$ | 3.6 | 0.05 | 1.07 | 1.18 | — |

In another experiment, a dosimetric evaluation of various field shaping devices was performed. Two field shapes were evaluated: a 5.5 cm diameter circle, and an anonymized clinical treatment field. In both cases, 3D printed frames were created and filled with 2 mm diameter tungsten BBs to a depth of 12 mm. These were compared to Cerrobend devices of the same shapes, which were 15 mm thick.

An ion chamber array (IC Profiler, Sun Nuclear, Melbourne, Fla., USA) was used to measure dose profiles of the cutouts with 6 MeV and 16 MeV. 300 monitor units (MU) were delivered for each profile measurement, using a Varian Clinac 21EX linear accelerator (Varian, Palo Alto, Calif.). The measured dose profiles were then compared to the TPS using the eMC algorithm (Varian eclipse v13.7, Palo Alto, Calif.), by importing the dose plane into the profiler software. Centering and full width half maximum (FWHM) metrics were taken directly from the profiler software.

Figure 3:
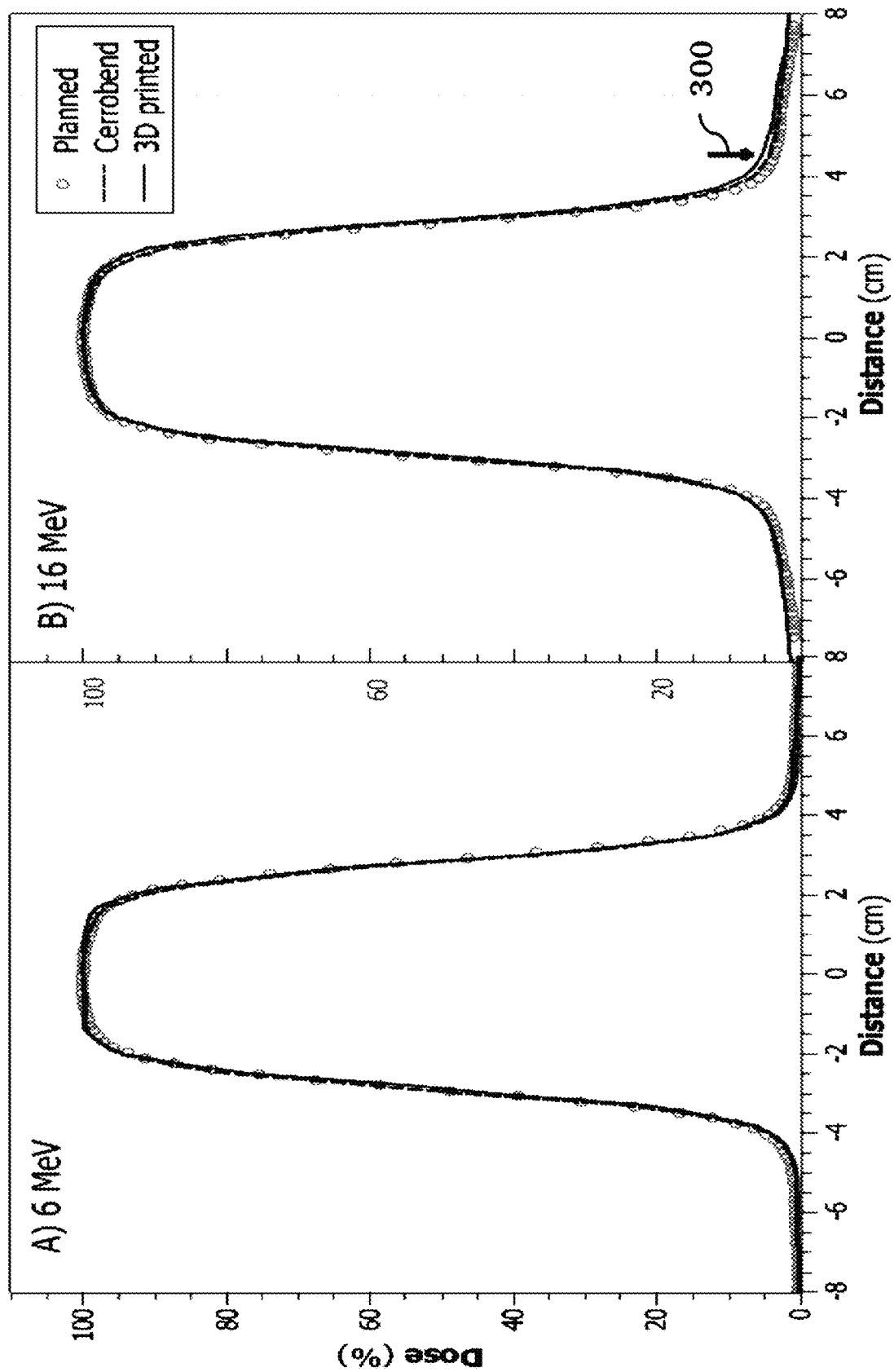
FIG. 3 shows crossline dose profile graphs of dose vs. distance, comparing a Cerrobend cutout (left) and a 3D printed cutout (right), according to an embodiment of the invention.

Crossline dose profiles of 6 MeV and 16 MeV electron beams delivered through the 5.5 cm circle of Cerrobend and 3D printed cutout are shown in FIG. 3 (10×10 cm$^2$ insert). The planned, Cerrobend, and 3D printed dose profiles (80% to 20% penumbra widths) agree within 0.4 mm. The comparisons between the FWHM, centering, and off-axis dose of the planned, Cerrobend and 3D printed cutouts are listed in Table 2. The FWHM for 3D printed circle, and the planned dose profile agreed within 1 mm. The centering of the Cerrobend circle was found to be up to 0.7 mm off center, compared to 0.1 mm and 0.3 mm for the 3D printed circle at 6 MeV and 16 MeV, respectively.

The dose profiles of 3D printed insert are centered better (0.1 mm and 0.3 mm for 6 MeV and 16 MeV, respectively) than that of Cerrobend insert (0.7±0.1 mm for both energies). For 6 MeV both inserts show less than 1% dose at 5 cm off-axis. For 16 MeV the planned dose is lower outside the radiation field than that of the measurements. The arrow 300 in FIG. 3 highlights the dose at 5 cm off-axis which is 4.1%, 3.5%, and 3.2% for the 3D printed insert, Cerrobend insert, and planned dose respectively. FWHM of the 3D printed, Cerrobend, and planned dose profiles are comparable with both energies.

Figure 5:
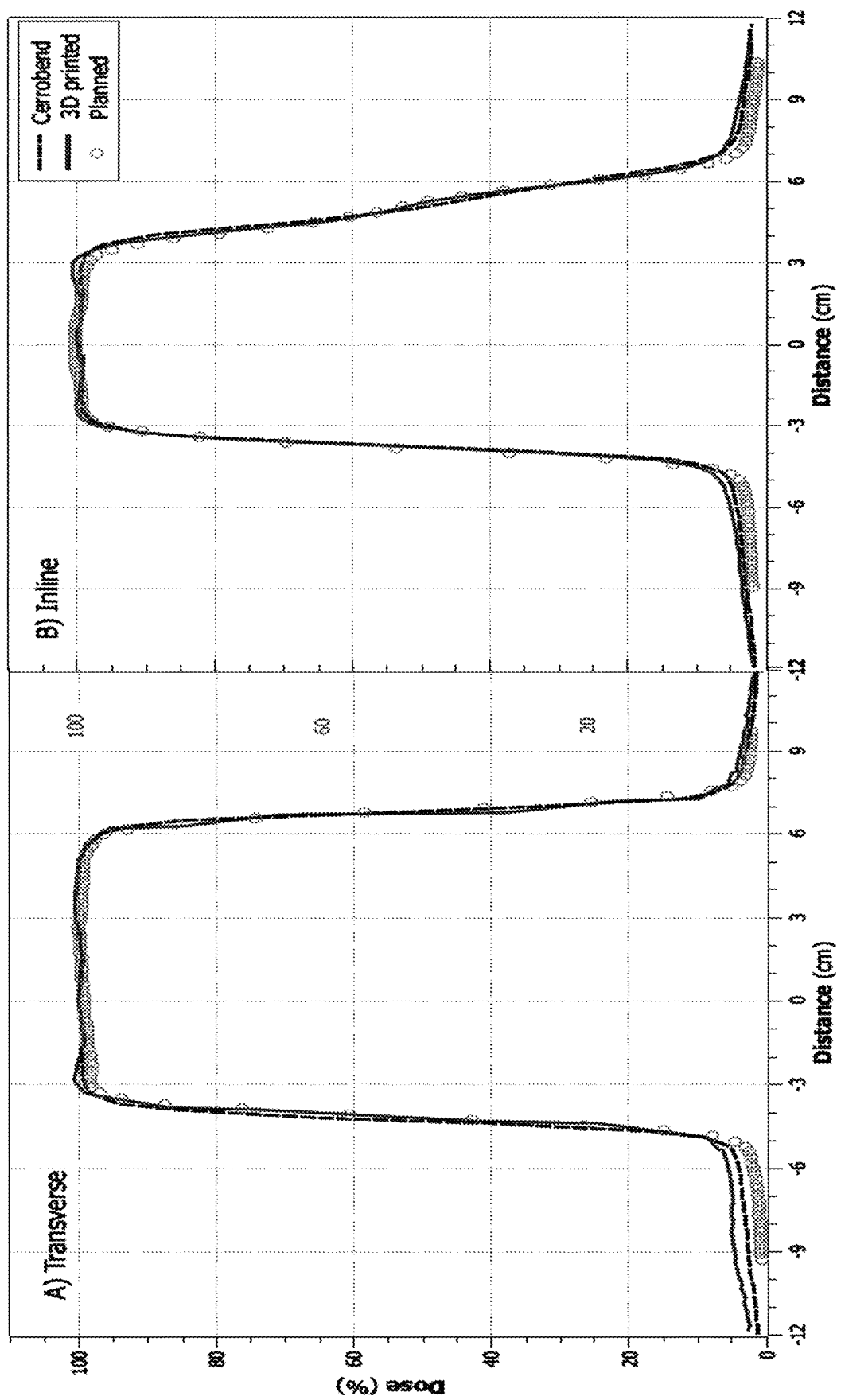
FIG. 5 shows transverse and inline dose profile graphs of dose vs. distance, comparing a Cerrobend cutout and a 3D printed cutout, according to an embodiment of the invention.

The dosimetric results for a clinically representative field shape are shown in FIG. 5, where the two graphs show transverse (left) and inline (right) dose profiles of 16 MeV beam through the Cerrobend and 3D printed cutouts measured with an IC profiler array at a 2.7 cm water equivalent depth. Also shown is the planned dose in a water phantom calculated from the eclipse treatment planning system using the eMC dose calculation algorithm.

Table 2 shows measured centering and width of profiles from a Sun nuclear profiler 2 detector aligned to light field crosshairs on a Varian True beam linear accelerator. For comparison, the planned dose plane was imported and compared in the same profiler software.

In some embodiments, out-of-field dose caused by electron scatter from the plastic walls of the 3D printed cutouts may be mitigated by 3D printing a dense metal shell or by making thinner plastic walls.

Figure 2:
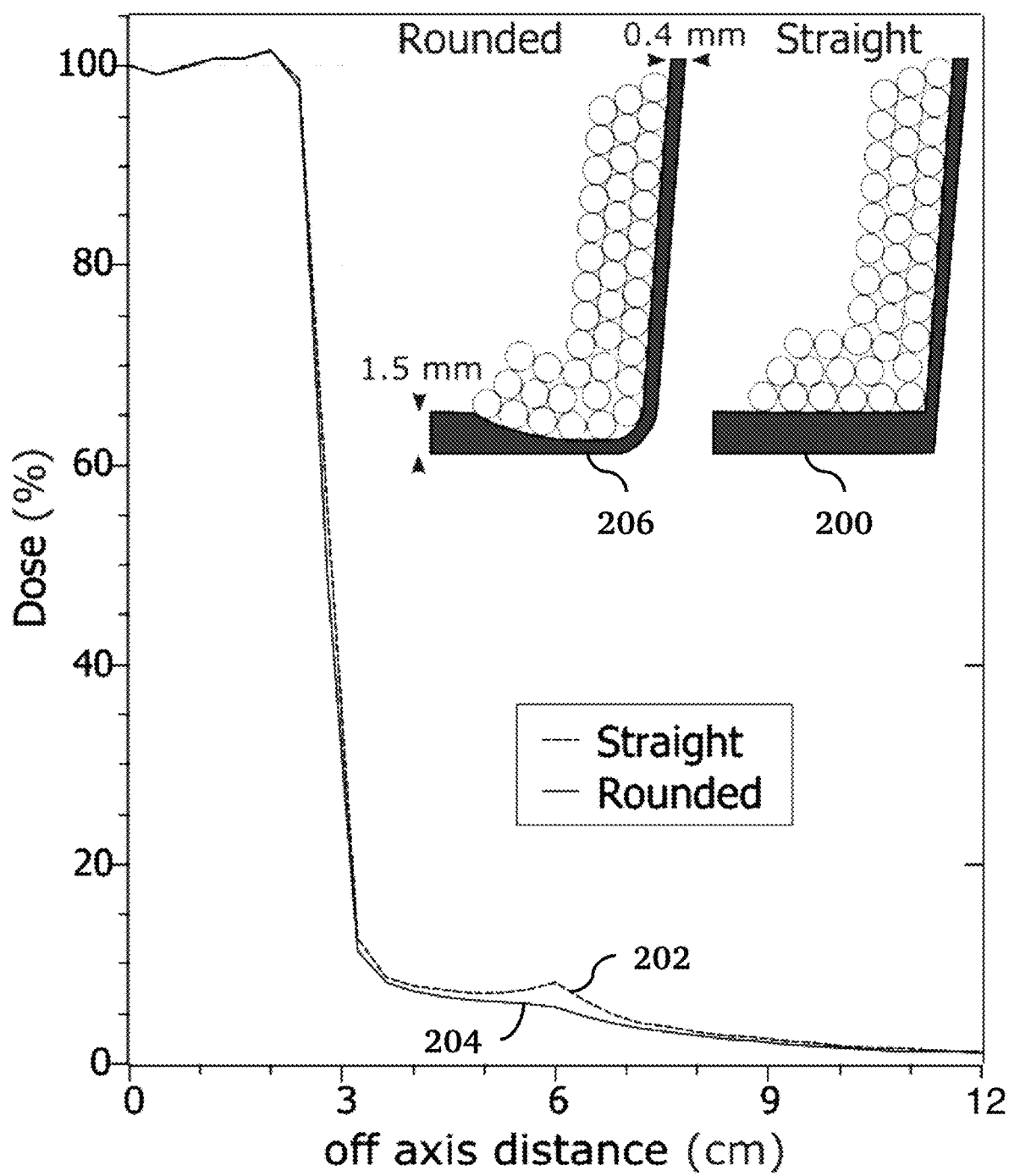
FIG. 2 is a graph of dose vs. off-axis distance, comparing a 3D printed insert having sharp corners and constant thickness walls with a 3D printed insert having rounded corners and variable thickness walls, according to an embodiment of the invention.

To reduce the amount of scatter from the plastic, the bottom of the insert is preferably designed to be thin in the areas close to the field. FIG. 2 is a graph comparing two 3D printed inserts with different cross section. The insert with the straight bottom 200, which has a constant thickness bottom, consistently produced a worse dose tail 202 than the dose tail 204 of the insert with rounded bottom 206, which has as thinned bottom close to the field. The slopes are to match the beam divergence. For clarity, only some BBs are shown in the figure. Other off-axis directions have the same dose profiles. The 2-8% dose in the out of field regions is comparable to that for Cerrobend cutouts.

In conclusion, the present invention provides a field shaping device that accurately reproduces the dose profiles of conventional Cerrobend cutouts. The design of this field shaping device avoids the need to use of toxic materials in the clinic, reduces manual labor, and provides improved reproduction of the field placement and field shape compared to Cerrobend.

The invention claimed is:

1. An electron beam field shaping device comprising:
a frame having a bottom, outer side walls, an opening in the bottom, and inner side walls around the opening in the bottom, where the outer side walls, the bottom, and the inner side walls define an interior space of the frame;
where the bottom has a variable thickness and rounded corners;
where the frame has a shape compatible for mounting in an electron applicator on a linear accelerator;
a granular material contained within the interior space, where the granular material has a bulk density of at least 3 g/cm$^3$ and composed of metal grains having a size between 1 μm and 4 mm.

2. The electron beam field shaping device of claim 1 where the frame is composed of a 3D printable material with a Youngs modulus greater than 0.5 GPa.

3. The electron beam field shaping device of claim 1 where the inner side walls are 0.2-5 mm thick and 5-30 mm tall.

4. The electron beam field shaping device of claim 1 where the granular material contained within the interior space forms a 5-30 mm thick layer.

5. The electron beam field shaping device of claim 1 where the metal grains are solid tungsten alloy ball bearings 1-4 mm in diameter.

TABLE 2

| | 6 MeV | | | 16 MeV | | | Physical Size Measurements Insert | |
|---|---|---|---|---|---|---|---|---|
| Insert type | FWHM (cm) | Center (cm) | Dose 5 cm off axis | FWHM (cm) | Center (cm) | Dose 5 cm off axis | Average diameter (cm) | diameter variation (cm) |
| 3D printed | 5.70 | 0.01 | 0.95% | 5.77 | −0.03 | 4.1% | 5.46 | 0.03 |
| Cerrobend | 5.71 | −0.07 | 0.8% | 5.78 | −0.06 | 3.5% | 5.44 | 0.08 |
| planned | 5.77 | N/A | 0.50% | 5.77 | N/A | 3.2% | N/A | N/A |

6. The electron beam field shaping device of claim 1 where the metal grains are composed of a powder selected from the group consisting of tungsten alloy powder and aluminum oxide powder.

\* \* \* \* \*